United States Patent
Edelman et al.

(10) Patent No.: US 9,597,435 B2
(45) Date of Patent: Mar. 21, 2017

(54) MEDICAL DEVICES HAVING A BIORESORBABLE COATING LAYER WITH A PRE-DETERMINED PATTERN FOR FRAGMENTATION

(75) Inventors: Peter Edelman, Maple Grove, MN (US); Afsar Ali, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1223 days.

(21) Appl. No.: 12/434,856

(22) Filed: May 4, 2009

(65) Prior Publication Data
US 2009/0274743 A1 Nov. 5, 2009

Related U.S. Application Data

(60) Provisional application No. 61/050,449, filed on May 5, 2008.

(51) Int. Cl.
| | |
|---|---|
| *A61F 2/00* | (2006.01) |
| *A61L 31/14* | (2006.01) |
| *A61L 31/10* | (2006.01) |
| *A61L 31/16* | (2006.01) |

(52) U.S. Cl.
CPC .............. *A61L 31/148* (2013.01); *A61L 31/10* (2013.01); *A61L 31/16* (2013.01); *A61L 2300/00* (2013.01)

(58) Field of Classification Search
CPC .............. A61F 13/15203; A61F 13/511; A61F 13/51305; A61L 2300/00; A61L 31/10; A61L 31/148; A61L 31/16
See application file for complete search history.

(56) References Cited

U.S. PATENT DOCUMENTS

| | | |
|---|---|---|
| 6,827,737 B2 | 12/2004 | Hill et al. |
| 6,873,087 B1 * | 3/2005 | Choi et al. ............... 310/323.17 |
| 2003/0028240 A1 * | 2/2003 | Nolting et al. ............. 623/1.13 |
| 2005/0055078 A1 * | 3/2005 | Campbell .................... 623/1.11 |
| 2005/0087520 A1 | 4/2005 | Wang et al. |
| 2005/0171593 A1 | 8/2005 | Whirley et al. |
| 2005/0208100 A1 * | 9/2005 | Weber et al. ................. 424/426 |
| 2006/0088567 A1 | 4/2006 | Warner et al. |
| 2006/0155370 A1 | 7/2006 | Brister |
| 2007/0231850 A1 * | 10/2007 | Geoffrey et al. ............... 435/29 |
| 2008/0014332 A1 | 1/2008 | Castro et al. |
| 2008/0073505 A1 * | 3/2008 | Niu et al. ...................... 250/288 |

OTHER PUBLICATIONS

Christopher A Mills, Melba Navarro, Elisabeth Engel, Elena Martinez, Maria Pau Ginebra, Josep Planell, Abdelhamid Errachid, Josep Samitier. Transparent micro- and nanopatterned poly(lactic acid) for biomedical applications. Journal of Biomedical Materials Research Part A (2006) vol. 76, Issue: 4, pp. 781-787.*
Andrew L. Hook, Helmut Thissen and Nicolas H. Voelcker. Surface manipulation of biomolecules for cell microarray applications. Trends in Biotechnology vol. 24, Issue 10, Oct. 2006, pp. 471-477.*
Y. Lu, S.C. Chen. Micro and nano-fabrication of biodegradable polymers for drug delivery. Advanced Drug Delivery Reviews 56 (2004) 1621-1633.*
L Jay Guo. Recent progress in nanoimprint technology and its applications (Review Article). 2004 J. Phys. D: Appl. Phys. 37(1): R123-R141.*
Thomas Glinsner and Gerald Kreindl. in:Lithography(Ed. By Michael Wang). Chapter 24. Nanoimprint Lithography(2010) pp. 495-516.*
Christopher A. Mills; Melba Navarro; Elisabeth Engel; Elena Martinez; Maria Pau Ginebra; Josep Planell; Abdelhamid Errachid; Josep Samitier. Transparent micro- and nanopatterned poly(lactic acid) for biomedical applications. Journal of Biomedical Materials Research Part A (2006) 76(4):781-787.*
Mills et al. Transparent micro- and nanopatterned poly(lactic acid) for biomedical applications. Journal of Biomedical Materials Research Part A (2006) 76(4):781-787.*
Lan et al. Nanoimprint Lithography. in: "Lithography", edited by Michael Wang, 2010. Chapter 23, p. 457-494 (and references therein).*
McMurray et al. Nanopatterned Surfaces for Biomedical Applications. in: Biomedical Engineering, Trends in Materials Science, edited by Anthony N. Laskovski, 2011, 564 pages. Chapter 16, pp. 375-396 (and references therein).*
Caves et al. The evolving impact of microfabrication and nanotechnology on stent design. Journal of vascular surgery (2006), vol. 44(6):1363-1368.*
Wilkinson et al., Nanofabrication in cellular engineering. J. Vac. Sci. Technol. B 16, 3132 (1998).*
International Search Report and Written Opinion of the International Searching Authority, dated Jul. 2, 2010, from related International Application No. PCT/US2009/042666.

* cited by examiner

*Primary Examiner* — Robert A Wax
*Assistant Examiner* — Olga V Tcherkasskaya
(74) *Attorney, Agent, or Firm* — Seager, Tufte & Wickhem, LLP

(57) ABSTRACT

Intravascular medical devices comprising a coating layer disposed on a substrate associated with the medical device, wherein the coating layer has a pre-determined fragmentation pattern. At least a portion of the coating layer comprises a plurality of discontinuous bioresorbable members, wherein the discontinuous bioresorbable members have a size less than the luminal diameter of an arteriole. The coating layer may be formed by excavating portions of a coating layer (e.g., by laser ablation) to create gaps which define the discontinuous bioresorbable members. In certain embodiments, the coating layer is formed of a heat-bondable material. In such embodiments, the discontinuous bioresorbable members may be adhered to the substrate via heat bonds. Also disclosed are methods of forming a coating layer on medical devices and methods of treating intravascular sites.

28 Claims, 4 Drawing Sheets

MEDICAL DEVICES HAVING A BIORESORBABLE COATING LAYER WITH A PRE-DETERMINED PATTERN FOR FRAGMENTATION

CROSS REFERENCE TO RELATED APPLICATION

The present application claims priority to U.S. provisional application Ser. No. 61/050,449 filed May 5, 2008, the disclosure of which is incorporated herein by reference in its entirety.

TECHNICAL FIELD

The present invention relates to medical devices, and in particular, medical devices having a bioresorbable coating.

BACKGROUND

Many medical devices have a coating to improve the therapeutic effectiveness of the device. For example, some vascular stents having a coating containing a drug which is eluted from the stent for treatment of the vessel and/or to prevent some of the unwanted effects and complications of implanting the stent. Although various coatings for stents have been proposed, there is a continuing desire for improved coatings for stents.

SUMMARY

In one aspect, the present invention provides an intravascular medical device comprising a coating layer disposed on a substrate associated with the medical device, wherein at least a portion of the coating layer comprises a plurality of discontinuous bioresorbable members, and wherein the discontinuous bioresorbable members have a size less than the luminal diameter of an arteriole.

In other aspects, the present invention also provides methods for forming a coating layer on medical devices and methods for treating an intravascular site.

BRIEF DESCRIPTION OF THE DRAWINGS

FIG. 1A shows a top view of a strut of the stent. FIG. 1B shows a cross-section side view of a portion of the stent strut in FIG. 1A. FIG. 1C shows the stent implanted in an artery.

DETAILED DESCRIPTION

Figure 1A:
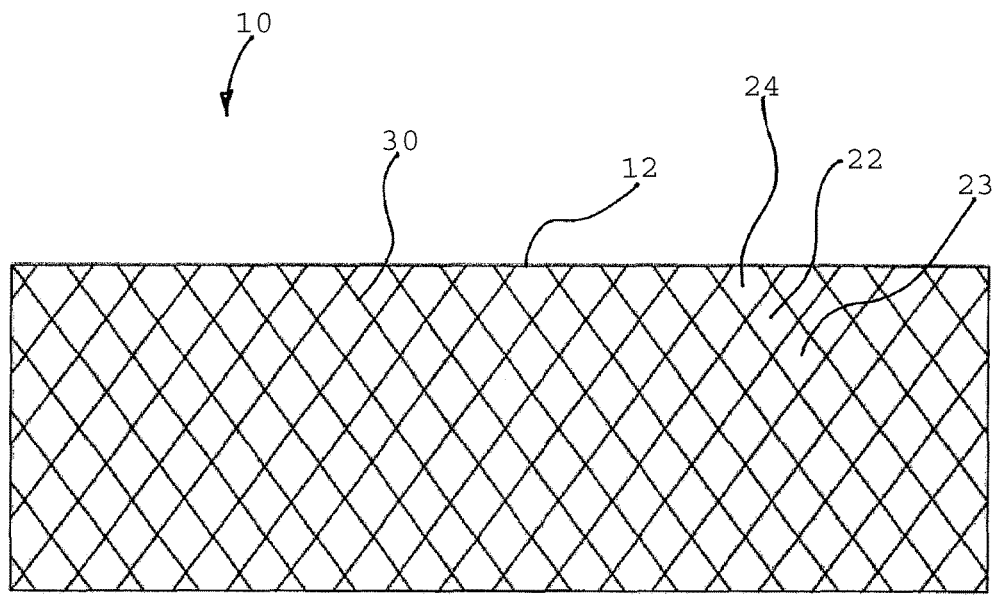
FIGS. 1A-1C show various views of a stent according to an embodiment of the present invention.

In one aspect, the present invention provides an intravascular medical device comprising a coating layer disposed on a substrate associated with the medical device, wherein the coating layer has a pre-determined pattern which can allow a more controlled fragmentation of the coating layer. The coating layer may comprise any of various bioresorbable materials that can be used in medical device coatings. As used herein, the term "bioresorbable" is intended to mean biodegradable and/or bioresorbable. For example, the coating layer may comprise a biodegradable polymer or a bioresorbable inorganic material. The material used for the coating layer may be applied to the medical device using any of various coating techniques that can be used for coating medical devices. The substrate may be a surface of the medical device or another coating over the medical device (i.e., the coating layer may be part of a multi-layered coating). A therapeutic agent may be contained in the coating layer, in another coating on the medical device, or another part of the medical device (e.g., in cavities within the surface of the medical device).

At least a portion of the coating layer is partitioned into a plurality of discontinuous members. As used herein, "discontinuous members" refers to discrete portions of a coating layer that are defined by gaps extending through the full thickness of the coating layer. These gaps, which separate the discontinuous members from each other, may be formed by excavating portions of the coating layer using any of various techniques which remove material in a manner that controls the size, shape, and location of the gaps. For example, such techniques include direct-write etching using energetic beams (e.g., laser, ion, or electron), micromachining, microdrilling, or lithographic processes.

The discontinuous members have a size less than the luminal diameter of an arteriole. This feature may be useful in situations where the coating layer becomes fragmented and detaches as it undergoes degradation in the body. For example, biodegradable coatings often undergo degradation through a bulk erosion process, in which the coating erodes uniformly throughout the bulk of the coating (as opposed to erosion only at the surface of the coating). This erosion process can lead to a loss of coating integrity and adhesion to the substrate. Additionally, as the degradable coating degrades, water uptake increases, which leads to swelling. This swelling can cause a decrease in adhesion due to lateral forces being transferred to the interface between the coating and the substrate. Thus, as the coating layer on the medical device degrades, any fragmentation of the coating layer will preferentially occur in a pre-determined fashion by detachment of the discontinuous members. Because of their size, the detached discontinuous members may avoid causing embolisms in blood vessels downstream of the medical device.

In general, the arterioles of human adults have a luminal diameter of about 20-30 μm. As such, in some cases, the discontinuous members have a size less than 30 μm; and in some cases, less than 10 μm. In some cases, the discontinuous members have a size in the range of 5 μm to 30 μm. In some cases, the discontinuous members have a size approximately that of a red blood cell or smaller. The size of the discontinuous members, as used herein, is intended to be measured along its longest axis.

Figure 1B:
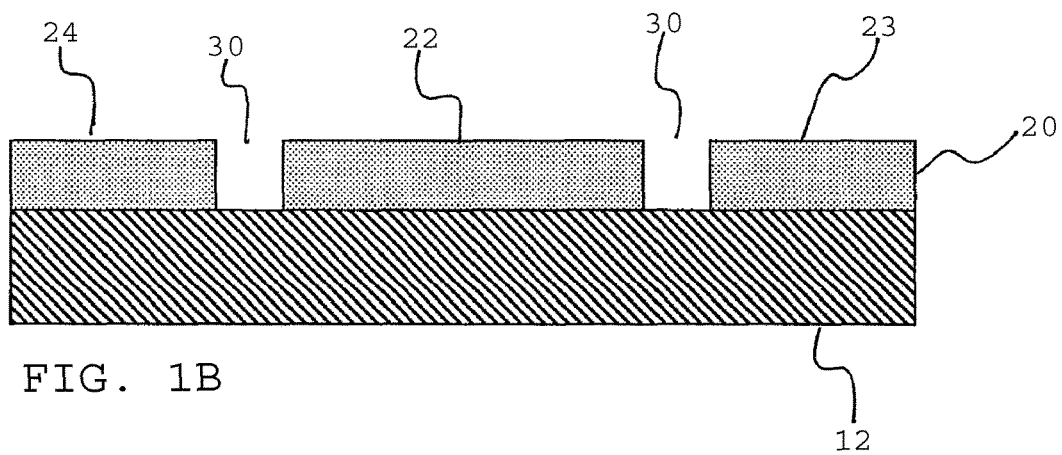
Figure 1C:
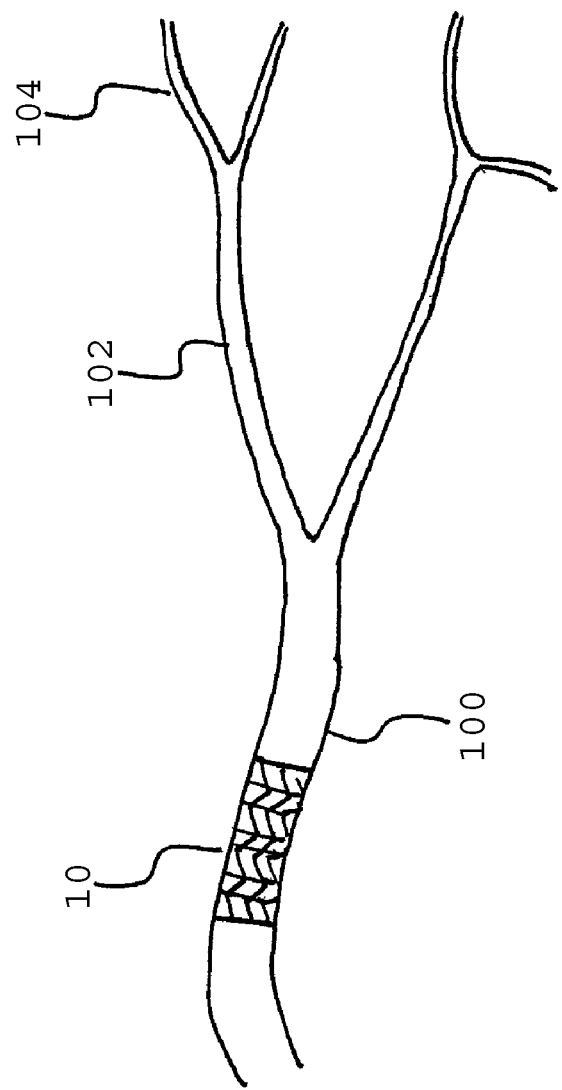

For example, referring to the embodiment shown in FIGS. 1A-1C, a stent strut 12 of a stent 10 has a coating layer 20 formed of a biodegradable polymer. Coating layer 20 contains a therapeutic agent dispersed therein, and comprises a plurality of discontinuous members arranged in a crosshatch pattern. The discontinuous members have a size less than the luminal diameter of an arteriole. FIG. 1B shows a cross-section side view of a portion of stent strut 12 containing discontinuous members 22, 23, and 24. These discontinuous members 22, 23, and 24 are separated from each other by gaps 30, which are created by laser ablation (e.g., using a UV excimer or Nd:Yag laser).

In operation, referring to FIG. 1C, stent 10 is delivered and implanted into the lumen of an artery 100. Located downstream of artery 100 are arterioles 102 and capillaries 104, which have luminal diameters smaller than that of artery 100. Should coating layer 20 undergo bulk erosion with fragmentation, the fragmentation will preferentially occur by detachment of the discontinuous members. Because these discontinuous members have a size less than the luminal diameter of an arteriole, the risk of downstream embolisms in arterioles 102 is reduced.

In certain embodiments, the coating layer is formed of a heat-bondable material. As used herein, "heat-bondable material" refers to a material which can be softened and/or made flowable by the application of heat, and then bonded to another material. For example, the heat-bondable material may be a polymer-containing material (such as thermoplastic polymers which flow when heated). The process of creating the discontinuous members in the coating layer can involve the application of heat to enhance the adhesion of the discontinuous members to the substrate. For example, localized heating of the coating layer and/or substrate by an energetic beam (e.g., a laser) used in the excavation process may result in the formation of heat bonds between the cooperating surfaces. Various amounts of heating may be used to create heat bonds between the coating layer and the substrate. In some cases, the temperature is high enough to re-mold or soften the heat-bondable material, but not enough to melt the heat-bondable material (e.g., heat staking). In some cases, the temperature is high enough to melt the heat-bondable material (e.g., spot welding). The amount of heating can be controlled by adjusting various parameters of the excavation process. For example, in the case of laser ablation, the amount of heat can be controlled by varying the wavelength, pulse frequency, and/or type of laser used.

Figure 2:
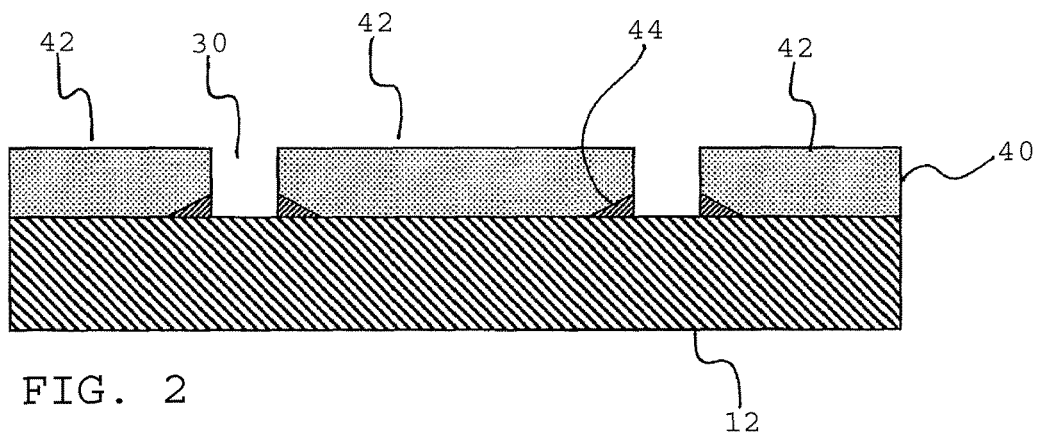
FIG. 2 shows a cross-section side view of a strut of a stent according to another embodiment.

For example, referring to the embodiment shown in FIG. 2, a stent strut 12 of a stent has a coating layer 40 formed of a biodegradable polymer. Coating layer 40 contains a therapeutic agent dispersed therein, and comprises discontinuous members 42 which have a size less than the luminal diameter of an arteriole. Discontinuous members 42 are separated from each other by gaps 30, which are created by laser ablation. The laser irradiation causes localized heating at the interface of discontinuous members 42 and the surface of stent strut 12 in the vicinity of gaps 30. This causes the formation of heat bonds 44, which strengthen the adhesion of discontinuous members 42 to stent strut 12.

In operation, the stent is delivered to an intravascular site and implanted therein. Because of heat bonds 44, discontinuous members 42 are resistant to detachment from the surface of stent strut 12. Nevertheless, should coating layer 40 undergo bulk erosion with fragmentation, the fragmentation will preferentially occur by detachment of discontinuous members 42. Because these discontinuous members 42 have a size less than the diameter of an arteriole, the risk of downstream embolisms is reduced.

Figure 3:
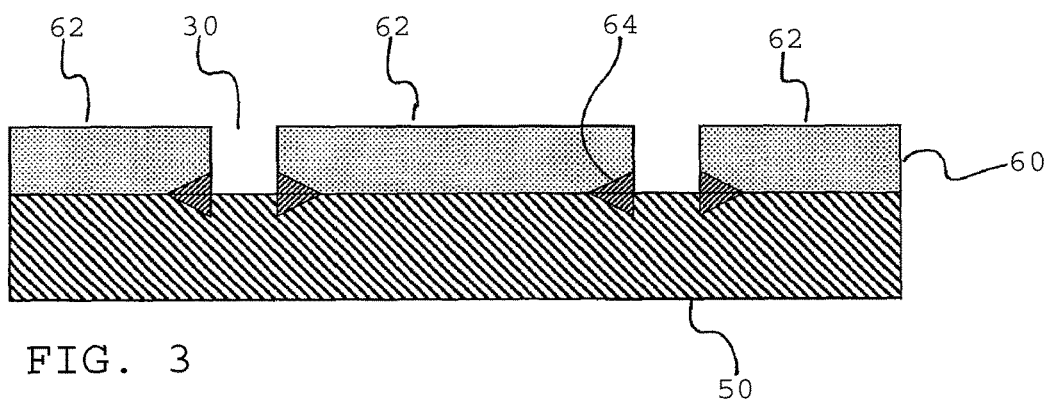
FIG. 3 shows a cross-section side view of a strut of a stent according to yet another embodiment.

In some cases, the substrate (as well as the coating layer) also comprises a heat-bondable material (e.g., a polymer-containing material). In such cases, the substrate may further participate in the formation of heat bonds. For example, referring to the embodiment shown in FIG. 3, a stent strut 50 of a stent has a coating layer 60 formed of a biodegradable polymer. Coating layer 60 contains a therapeutic agent dispersed therein, and comprises discontinuous members 62 which have a size less than the luminal diameter of an arteriole. In this particular embodiment, stent strut 50 is formed of a polymer-containing material. Discontinuous members 62 are separated from each other by gaps 30, which are created by laser ablation. The laser irradiation causes localized heating at the interface of discontinuous members 62 and the surface of stent strut 50 in the vicinity of gaps 30. This causes the formation of heat bonds 64 involving both the surface of stent strut 50 and discontinuous members 62.

In operation, the stent is delivered to an intravascular site and implanted therein. Because of heat bonds 64, discontinuous members 62 are resistant to detachment from the surface of stent strut 50. Nevertheless, should coating layer 60 undergo bulk erosion with fragmentation, the fragmentation will preferentially occur by detachment of discontinuous members 62. Because these discontinuous members 62 have a size less than the diameter of an arteriole, the risk of downstream embolisms is reduced.

Figure 4A:
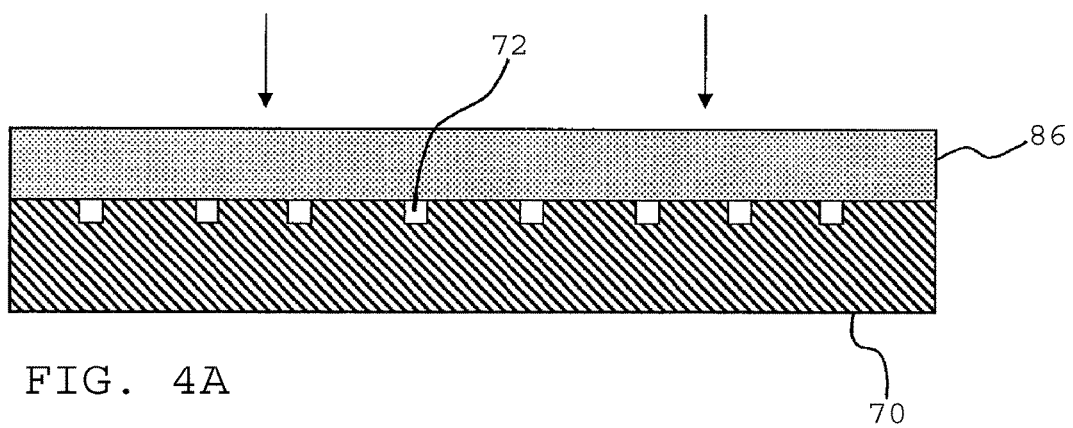
FIGS. 4A and 4B show cross-section side views of a strut of a stent according to yet another embodiment.
Figure 4B:
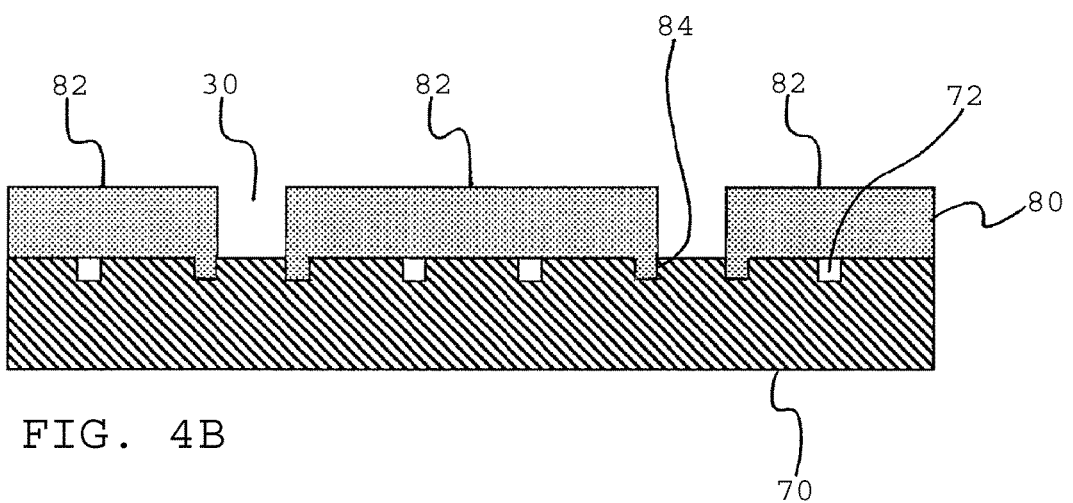

In some cases, the substrate has a surface that is non-smooth. For example, the substrate may have a rough or textured surface, or the substrate may have bumps, nodules, ridges, grains, protrusions, pits, holes, openings, perforations, cracks, fracture lines, pores, grooves, or channels on its surface. This feature may be useful in mechanically interlocking the coating layer with the substrate during the heat-bonding process. For example, referring to the embodiment shown in FIGS. 4A and 4B, a stent strut 70 of a stent has a coating layer 80 formed of a biodegradable polymer. Coating layer 80 contains a therapeutic agent dispersed therein. In this particular embodiment, stent strut 70 has a surface comprising a plurality of pits 72. Referring to FIG. 4A, a laser is used to ablate an unfragmented coating layer 86 at the locations indicated by the arrows. Referring to FIG. 4B, the laser ablation creates gaps 30 in unfragmented coating layer 86 so as to form a fragmented coating layer 80 having discontinuous members 82. Discontinuous members 82 have a size less than the luminal diameter of an arteriole. The laser irradiation causes localized heating at the interface of discontinuous members 82 and the surface of stent strut 70 in the vicinity of gaps 30. This localized area of heated polymer in discontinuous members 82 flows into pits 72 to create interlocking portions 84 of discontinuous member 82. By interlocking with the surface of stent strut 70, the adhesion between discontinuous members 82 and stent strut 70 is strengthened.

In operation, the stent is delivered to an intravascular site and implanted therein. By mechanically interlocking with the surface of stent strut 70, discontinuous members 82 are resistant to detachment from the surface of stent strut 70. Nevertheless, should coating layer 80 undergo bulk erosion with fragmentation, the fragmentation will preferentially occur by detachment of discontinuous members 82. Because these discontinuous members 82 have a size less than the diameter of an arteriole, the risk of downstream embolisms is reduced.

In embodiments where a therapeutic agent is contained in the coating layer, the spatial distribution, pattern, and/or sizes of the discontinuous members may be selected to vary the total dose and/or release profile of the therapeutic agent. For example, because a greater amount of the coating layer material may need to be excavated in order to create denser patterns or smaller discontinuous members, this may result in a coating layer having reduced capacity for containing the therapeutic agent. Further, the spatial distribution, pattern, and/or sizes of the discontinuous members in the coating layer at one portion of the medical device may differ from that of the discontinuous members in the coating layer at another portion of the medical device. This feature may be useful in providing different therapeutic agent release rates on different portions of the medical device. For example, a vascular stent may have a coating layer with larger discontinuous members at the end portions of the stent than at the intermediate portions of the stent to provide a higher release rate of the therapeutic agent at the ends of the stent, and thereby reduce the unwanted "edge-effect" that sometimes occurs with stent implantation. As an additional example, a stent designed to be implanted at a bifurcation may be made to provide a higher dose of therapeutic agent at the bifurcation area as compared to the non-bifurcation area of the vessel.

The intravascular medical device may be for implantation in the vascular system, insertion and travel through the vascular system, or temporary positioning in the vascular system. Non-limiting examples of intravascular medical devices that can be used with the present invention include stents, stent grafts, catheters, guide wires, neurovascular aneurysm coils, balloons, filters (e.g., vena cava filters), vascular grafts, intraluminal paving systems, pacemakers, electrodes, leads, defibrillators, intra-aortic balloon pumps, heart valves, sutures, artificial hearts, and other devices that are used in the vascular system.

The therapeutic agent used in the present invention may be any pharmaceutically acceptable agent, a biomolecule, a small molecule, or cells. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds have a molecular weight of less than 100 kD. Exemplary cells include stem cells, progenitor cells, endothelial cells, adult cardiomyocytes, and smooth muscle cells.

Non-limiting examples of biodegradable polymers suitable for use in the present invention include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly(lactic acid-co-glycolic acid), poly(DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropyl methyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc calcium phosphate.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. An intravascular medical device comprising:
a coating layer disposed on a substrate associated with the medical device;
wherein at least a portion of the coating layer comprises a plurality of discontinuous bioresorbable members that define a preferential pattern of fragmentation upon degradation of the coating layer, and wherein the discontinuous bioresorbable members have a size less than the luminal diameter of an arteriole.

2. The medical device of claim 1, wherein the discontinuous bioresorbable members have a size less than 30 µm.

3. The medical device of claim 1, wherein the discontinuous bioresorbable members have a size less than 10 µm.

4. The medical device of claim 1, wherein the discontinuous bioresorbable members have a size approximately that of a red blood cell or smaller.

5. The medical device of claim 1, wherein the substrate is another coating over a surface of the medical device.

6. The medical device of claim 1, wherein the substrate is a surface of the medical device.

7. The medical device of claim 1, wherein the coating layer comprises a polymer.

8. The medical device of claim 7, wherein the polymer is a bioresorbable polymer.

9. The medical device of claim 1, wherein the coating layer comprises a heat-bondable material.

10. The medical device of claim 9, wherein the substrate comprises a heat-bondable material.

11. The medical device of claim 10, wherein the substrate comprises a polymer.

12. The medical device of claim 9, wherein at least some of the discontinuous bioresorbable members have heat-bonded portions at the interface of the discontinuous bioresorbable members and the substrate.

13. The medical device of claim 1, wherein the substrate has a non-smooth surface.

14. The medical device of claim 13, wherein at least some of the discontinuous bioresorbable members have interlocking portions that mechanically interlock with the non-smooth surface of the substrate.

15. The medical device of claim 1, wherein the coating layer contains a therapeutic agent.

16. A method of forming a coating layer on a medical device, comprising:
disposing a coating layer on a substrate associated with the medical device; and
excavating portions of the coating layer to form a plurality of discontinuous bioresorbable members in the coating layer, wherein the discontinuous bioresorbable members define a preferential pattern of fragmentation upon degradation of the coating layer, and wherein the discontinuous bioresorbable members have a size less than the luminal diameter of an arteriole.

17. The method of claim 16, wherein the discontinuous bioresorbable members have a size less than 30 µm.

18. The method of claim 16, wherein the discontinuous bioresorbable members have a size less than 10 µm.

19. The method of claim 16, wherein the discontinuous bioresorbable members have a size approximately that of a red blood cell or smaller.

20. The method of claim 16, wherein the step of excavating is performed using an energetic beam.

21. The method of claim 20, wherein the coating layer comprises a heat-bondable material, and wherein the step of excavating further comprises heating a localized area of the coating layer and/or substrate.

22. The method of claim 21, wherein the step of heating the localized area results in the formation of heat bonds at the interface of the discontinuous bioresorbable members and the substrate.

23. A method of treating an intravascular site, comprising:
(a) providing a medical device comprising:
   a coating layer disposed on a substrate associated with the medical device;
   wherein at least a portion of the coating layer comprises a plurality of discontinuous bioresorbable members that define a preferential pattern of fragmentation upon degradation of the coating layer, and wherein the discontinuous bioresorbable members have a size less than the luminal diameter of an arteriole;
(b) delivering the medical device to the intravascular site.

24. The method of claim 23, wherein the step of delivering the medical device further comprises implanting the medical device at the intravascular site.

25. The method of claim 23, wherein the coating layer comprises a therapeutic agent.

26. The method of claim 23, wherein the discontinuous bioresorbable members have a size less than 30 μm.

27. The method of claim 23, wherein the discontinuous bioresorbable members have a size less than 10 μm.

28. The method of claim 23, wherein the discontinuous bioresorbable members have a size approximately that of a red blood cell or smaller.

\* \* \* \* \*